United States Patent [19]

Kurome et al.

[11] Patent Number: 5,572,993
[45] Date of Patent: Nov. 12, 1996

[54] APPARATUS FOR ASSISTING IN VENTILATING THE LUNGS OF A PATIENT

[75] Inventors: Kanji Kurome; Atsushi Asahina; Yoshihito Hashimoto; Yoshiki Nakagawa, all of Ibaraki; Harutomo Wakou, Sendai; Yoshitaka Oku, Sakyo-ku, all of Japan

[73] Assignee: Teijin Limited, Osaka, Japan

[21] Appl. No.: 498,751

[22] Filed: Jul. 6, 1995

[30] Foreign Application Priority Data

| Jul. 6, 1994 | [JP] | Japan | 6-154759 |
| Jul. 6, 1994 | [JP] | Japan | 6-154760 |
| Jul. 6, 1994 | [JP] | Japan | 6-154761 |
| Mar. 13, 1995 | [JP] | Japan | 7-052490 |

[51] Int. Cl.$^6$ ............................................. A61M 16/00
[52] U.S. Cl. ............................. 128/204.23; 128/205.25; 128/204.21
[58] Field of Search ...................... 128/204.18, 204.21, 128/204.23, 204.26, 205.24, 205.25

[56] References Cited

U.S. PATENT DOCUMENTS

| 3,910,270 | 10/1975 | Stewart | 128/204.24 |
| 4,031,885 | 6/1977 | Davis et al. | 128/720 |
| 4,682,591 | 7/1987 | Jones | 128/204.25 |
| 4,928,684 | 5/1990 | Breitenfelder et al. | 128/204.21 |
| 5,134,995 | 8/1992 | Gruenke et al. | 128/204.23 |
| 5,161,525 | 11/1992 | Kimm et al. | 128/204.26 |
| 5,239,995 | 8/1993 | Estes et al. | 128/204.23 |
| 5,293,875 | 3/1994 | Stone | 128/719 |
| 5,335,654 | 8/1994 | Rapoport | 128/204.23 |

FOREIGN PATENT DOCUMENTS

| A20452001 | 10/1991 | European Pat. Off. |
| 2554706 | 5/1985 | France |
| 3222963 | 10/1991 | Japan |
| 4231067 | 8/1992 | Japan |
| 5115554 | 5/1993 | Japan |
| 2077444 | 12/1981 | United Kingdom |
| WO-A8201654 | 5/1982 | WIPO |
| WO-A9406499 | 3/1994 | WIPO |

OTHER PUBLICATIONS

William W. Mushin, "Automatic Ventilation of the Lungs", 20 Feb. 1990, Balackwell Scientific Publications, Oxford London Edinburgh Melbourne, 166160, pp. 178–183.
William W. Mushin, "Automatic Ventilation of the Lungs", 20 Feb. 1990, Balackwell Scientific Publications, Oxford London Edinburgh Melbourne, 166160, pp. 152–158.

*Primary Examiner*—Edgar S. Burr
*Assistant Examiner*—Eric P. Raciti
*Attorney, Agent, or Firm*—Sughrue, Mion, Zinn, Macpeak & Seas

[57] ABSTRACT

An apparatus for assisting in ventilating the lungs of a patient comprises a respiratory gas source means; a breathing mask means; a conduit means for fluidly connecting the respiratory gas source means to the mask; a means fop regulating the pressure within the conduit means; a flow meter means for detecting the flow rate of the respiratory gas; and a pressure sensor means for detecting the pressure within the conduit adjacent to the breathing mask. The apparatus further comprises a means for calculating the flow impedance parameter of the flow system downstream the pressure sensing means; a means for storing the relationship between the operation of the pressure regulating means, the flow impedance parameter, and the pressure within the conduit means; a means for predicting the flow impedance parameter after a predetermined time interval; and a means for generating a target pressure to which the pressure regulating means regulates the pressure within the conduit. The pressure regulating means is controlled such that the pressure within the conduit adjacent to the breathing mask is substantially the target pressure based on the predicted flow impedance parameter and the data.

21 Claims, 14 Drawing Sheets

APPARATUS FOR ASSISTING IN VENTILATING THE LUNGS OF A PATIENT

BACKGROUND OF THE INVENTION (1) Field of the Invention

The invention relates to an apparatus for assisting in ventilating the lungs of a patient who cannot sustain enough respiration due to, for example, sleep apnea syndrome.

(2) Description of the Related Art

A number of devices are provided for assisting in ventilating the lungs of a patient who cannot sustain enough respiration due to, for example, sleep apnea syndrome. U.S. Pat. No. 4,655,213 describes an apparatus for treatment of sleep apnea syndrome by providing continuous positive airway pressure (CPAP) to maintain the airway of the patient in a continuously open state during sleep. However, the apparatus of U.S. Pat. No. '213 cannot assist the ventilation of the lungs of a patient sufficiently, since the described device provides the continuous positive airway pressure even during the expiration phase.

In order to solve the above problem, a ventilator described in Japanese Unexamined Patent Publication (Kokai) No. 53-16238 supplies respiratory gas to a patient at predetermined high and low pressure alternatively at a predetermined time interval. However, the ventilator of JPP '238 also cannot assist the ventilation of the lungs of a patient sufficiently, since it provides high and low pressure respiratory gas at the predetermined time interval while the respiratory cycle of a patient is not constant.

Japanese Examined Patent Publication (Kokoku) No. 50-38435 describes a respiration assisting device which detects the pressure of respiratory gas within a conduit between a respiratory gas source and a mask on the patient, and provides predetermined high and low pressure alternatively based on the detected pressure. On the other hand, Japanese Unexamined Patent Publication (Kokai) No. 3-222963 and Japanese Unexamined Patent Publication (Kokai) No. 4-231067 describe ventilators which control the flow of respiratory gas to a patient by detecting the flow rate so as to provide a predetermined high pressure when the detected flow rate to the patient higher than a predetermined reference flow rate, and predetermined low pressure when the detected flow rate is lower than the reference flow rate. A patient using such an apparatus will feel discomfort since the pressures required for the inspiration and expiration phase are not constant high and low pressure, and drastically change during the respective inspiration and expiration phase as well as the transition phase therebetween. Furthermore, in order to change the pressure or the flow rate, the patient must make a considerable expiratory effort against the respiratory gas flow from the respiratory gas source.

European Patent Publication No. 0,452,001 A2 describes a ventilator which controls the pressure of the respiratory gas such that the delivered pressure is directly proportional to the effort of the patient in consideration with the elastance and the flow resistance of the respiratory organ of the patient. The ventilator can control the pressure to the respiratory system including the ventilating apparatus. The ventilator also controls the flow rate of the respiratory gas and the pressure within the conduit between the respiratory gas source and the mask on the patient based on the detected flow rate. Thus, there is the same problem as the above-mentioned prior art, that is, patient must make a considerable expiratory effort against the respiratory gas flow from the respiratory gas source.

Japanese Unexamined Patent Publication (Kokai) No. 4-263876 described a ventilator which controls the respiratory gas flow to the patient by using closed-loop control or feedback control. In general, a ventilator which includes a respiratory gas source, a mask on a patient, a conduit between the respiratory gas source and the mask, and means for adjusting the pressure within the conduit to changeable target pressure forms a system with time lag. In even proportional assist ventilation, the patient will feel discomfort if the pressure of the respiratory gas is controlled at intervals of not less than 100 msec. However, open-loop control is not suitable for such a system due to the delay or inaccuracy of the control.

SUMMARY OF THE INVENTION

The invention is directed to solve the above mentioned problems of the prior art.

According to the invention, there is provided an apparatus for assisting in ventilating the lungs of a patient. The apparatus comprises a respiratory gas source means for supplying the respiratory gas to the patient; a breathing mask means for introducing the respiratory gas into the lungs of the patient, the breathing mask being put on the face of the patient; a conduit means for fluidly connecting the respiratory gas source means to the breathing mask for delivering the respiratory gas from the respiratory gas source means to the breathing mask; a means for regulating the pressure within the conduit means; a flow meter means for detecting the flow rate of the respiratory gas from the respiratory gas source to the breathing mask; a pressure sensor means for detecting the pressure within the conduit adjacent to the breathing mask. According to the feature of the invention, the apparatus further comprises a means for obtaining a flow impedance parameter of the flow system downstream of the pressure sensing means including the airway and the lungs of the patient based on the detected flow rate and pressure by the flow meter and the pressure sensor means; a means for storing the relationship between the operation of the pressure regulating means, the flow impedance parameter, and the pressure within the conduit means; a means for predicting the flow impedance parameter after a predetermined time interval; a means for generating a target pressure signal to which the pressure regulating means regulates the pressure within the conduit; and a means for controlling the operation of the pressure regulating means such that the pressure within the conduit adjacent to the breathing mask becomes substantially the target pressure based on the predicted flow impedance parameter and the relationship between the operation of the pressure regulating means, the flow impedance parameter, and the pressure within the conduit means.

In the invention, the pressure regulating means is controlled so that the pressure within the conduit adjacent to the breathing mask is the target pressure based on prediction and not on feed-back control.

The flow impedance parameter is preferably defined by the following equation.

$$\alpha = \frac{P^{1/2}}{Q}$$

where

α: flow impedance parameter
P: pressure within the conduit
Q: flow rate of the respiratory gas In one embodiment of the invention, the means for predicting the flow impedance parameter comprises a means for storing a preceding value of the flow impedance parameter and the present value of the flow impedance parameter. The predicted flow impedance parameter can be calculated by a first order extrapolation based on the preceding and present values of the flow impedance parameter.

In another embodiment, the means for predicting the flow impedance parameter comprises a means for storing a plurality of preceding values of the parameter and the present value of the flow impedance parameter. The predicted flow impedance parameter can be calculated by a second order extrapolation. Further, the predicted flow impedance parameter can be calculated by an extrapolation higher than the second order based on the plurality of preceding values and the present value of the flow impedance parameter.

The apparatus of the invention may further comprise a means for determing whether the respiration is in the expiration phase or in the inspiration phase.

In another embodiment of the invention, the means for determing the respiration phase comprises a means for comparing the pressure detected by the pressure sensor means with the target pressure; a means for differentiating the flow rate of the respiratory gas; a means for comparing the differential flow rate with a predetermined value. In this embodiment, the expiration phase is determined when the detected pressure is higher than the target pressure and the differential flow rate is lower than the predetermined value.

Further, in another embodiment, the means for determing the respiration phase comprises a means for comparing the pressure detected by the pressure sensor means with the target pressure; a means for differentiating the flow rate of the respiratory gas; a means for comparing the differential flow rate with a predetermined value; a means for differentiating the pressure detected by the pressure sensor; and a means for comparing the differential pressure with a predetermined value. In this embodiment, the expiration phase is determined when the detected pressure is higher than the target pressure, the differential flow rate is lower than the predetermined value, and the differential pressure is higher than the predetermined value.

According to another embodiment of the invention, the apparatus may further comprise an expiratory valve means, for exhausting the expiratory gas from the patient, provided in the conduit means downstream of the pressure regulating means, and a means for comparing the detected pressure by the pressure sensor means with a predetermined pressure level. Preferably, the expiratory valve means comprises a first expiratory valve provided in the conduit means downstream of and near the pressure regulating means, and a second expiratory valve provided in the conduit means upstream of the pressure sensor means and nearby the breathing mask. The first expiratory valve is open during the expiration phase. The second expiratory valve means is open when the expiration phase is initiated and is closed when the detected pressure is lower than the predetermined pressure level.

In the preferred embodiment of the invention, the pressure regulating means comprises a motor operated butterfly valve provided in the conduit means. The butterfly valve is closed when the expiration phase is initiated. After the initiation of the expiration phase, the butterfly valve may be kept closed until the detected pressure becomes lower than the predetermined level. After the detected pressure becomes lower than the predetermined level, the degree of the butterfly valve is controlled. The degree of the butterfly valve is also controlled during the inspiration phase.

DESCRIPTION OF THE PREFERRED EMBODIMENTS

Figure 1:
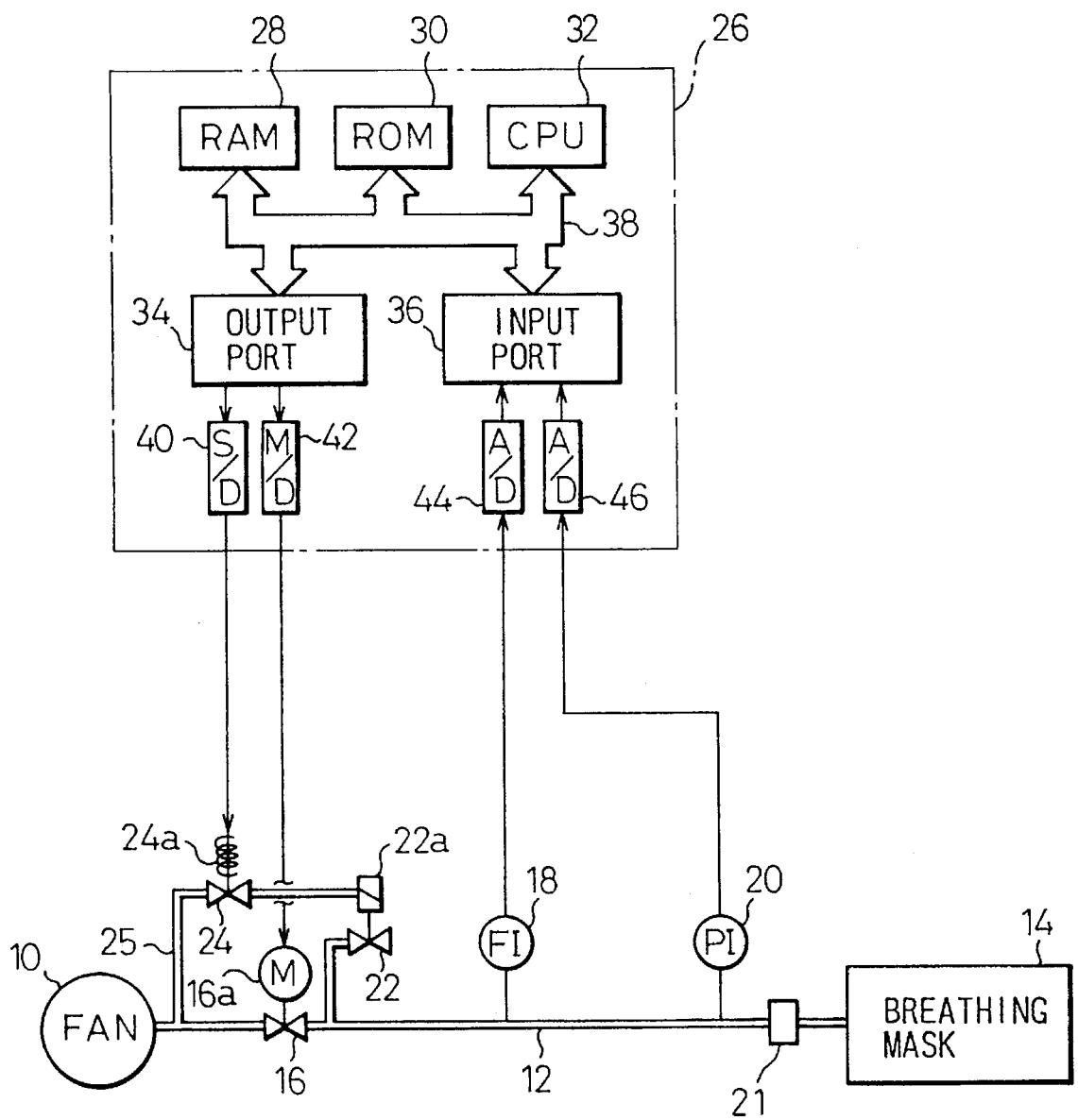
FIG. 1 is a schematic of an apparatus for ventilating the lungs of a patient according to the preferable embodiment of the invention.

With reference to FIG. 1, an apparatus for assisting in ventilating the lungs of a patient according to the first embodiment of the invention is shown. The patient cannot sustain enough respiration due to, for example, sleep apnea syndrome. The device comprises a fan 10 as a respiratory gas source to supply respiratory gas, in this embodiment air, a breathing mask 14 to be put on the face of a patient, and an respiratory gas conduit 12 provided between the fan 10 and the breathing mask 14. The respiratory gas source may be a blower or a pressurized tank which contains appropriate gas, such as air or oxygen. Further, the respiratory gas conduit 12 may be a hose, pipe or tube.

The device further comprises a pressure regulating valve 16 such as a motor operated butterfly valve provided in the respiratory gas conduit 12 to control the pressure within the respiratory gas conduit 12. The pressure regulating valve 16 uses a driving motor such as a stepping motor 16a which is electrically connected to a control unit 26 of the device as described hereinafter.

A main expiratory valve 22 such as a piston operated shut-off valve is provided in the conduit 12 downstream of the pressure regulating valve 16. The main expiratory valve 22 has a piston 22a for operating the main expiratory valve 22 between the open and the closed positions. The piston 22a is connected to the conduit 12 upstream of the pressure regulating valve 16 through a branch conduit 25. The pressure within the conduit 12 is effectively reduced when the main expiratory valve 22 is open.

A solenoid operated shut-off valve 24 is provided in the branch conduit 25 between the conduit 12 and the piston 22a. The solenoid operated shut-off valve 24 has a solenoid 24a which is electrically connected to the control unit 26, The solenoid operated valve 24 can operatively move between the open and the closed positions. When the solenoid 24a is energized, the solenoid operated shut-off valve 24 moves to the open position where the pressure within the conduit 12 upstream of the pressure regulating valve 16 is applied to the piston 22a to open the main expiratory valve 22. When the solenoid 24a is deenergized, the solenoid operated shut-off valve 24 moves to the closed position where the piston 22a is separated from the conduit 12 to close the main expiratory valve 22.

A flow meter 18 such as a hot wire type flow meter or a vane type flow meter is provided in the conduit downstream of the pressure regulating valve 16. The flow meter 18 is also electrically connected to the control unit 26. The flow meter detects the flow rate of the respiratory gas within the conduit 12 and generates an electrical signal, proportional to the detected flow rate, to the control unit 26.

Further, a pressure sensor 20 such as a semiconductor type pressure sensor is provided in the conduit adjacent to the breathing mask 14. The pressure sensor 20 is electrically connected to the control unit 26 and generates an electrical signal, proportional to the detected pressure of the respiratory gas adjacent to the breathing mask 14, to the control unit 26.

Further, an expiratory port 21 is provided between the pressure sensor 20 and the breathing mask 14 for providing a continuous leak path in the flow system. The expiratory port 21 may be a Whisper Swivel (registered trade mark) which is a product of RESPIRONICS INC, 1001 Murry Ridge Drive, Murrysville, Pa.

The control unit 26 comprises a random access memory (RAM) 28, a read only memory (ROM) 30, a central processing unit (CPU) 32, an output port 34, and an input port 36 which are connected to each other by a bidirectional bus 38. The solenoid 24a is connected to the output port 34 through a solenoid driver 40. The stepping motor 16a is connected to the output port 34 through a motor driver 42. The flow meter 18 and the pressure sensor 20 are connected to the input port 36 through A/D converters 44 and 46.

Figure 2:
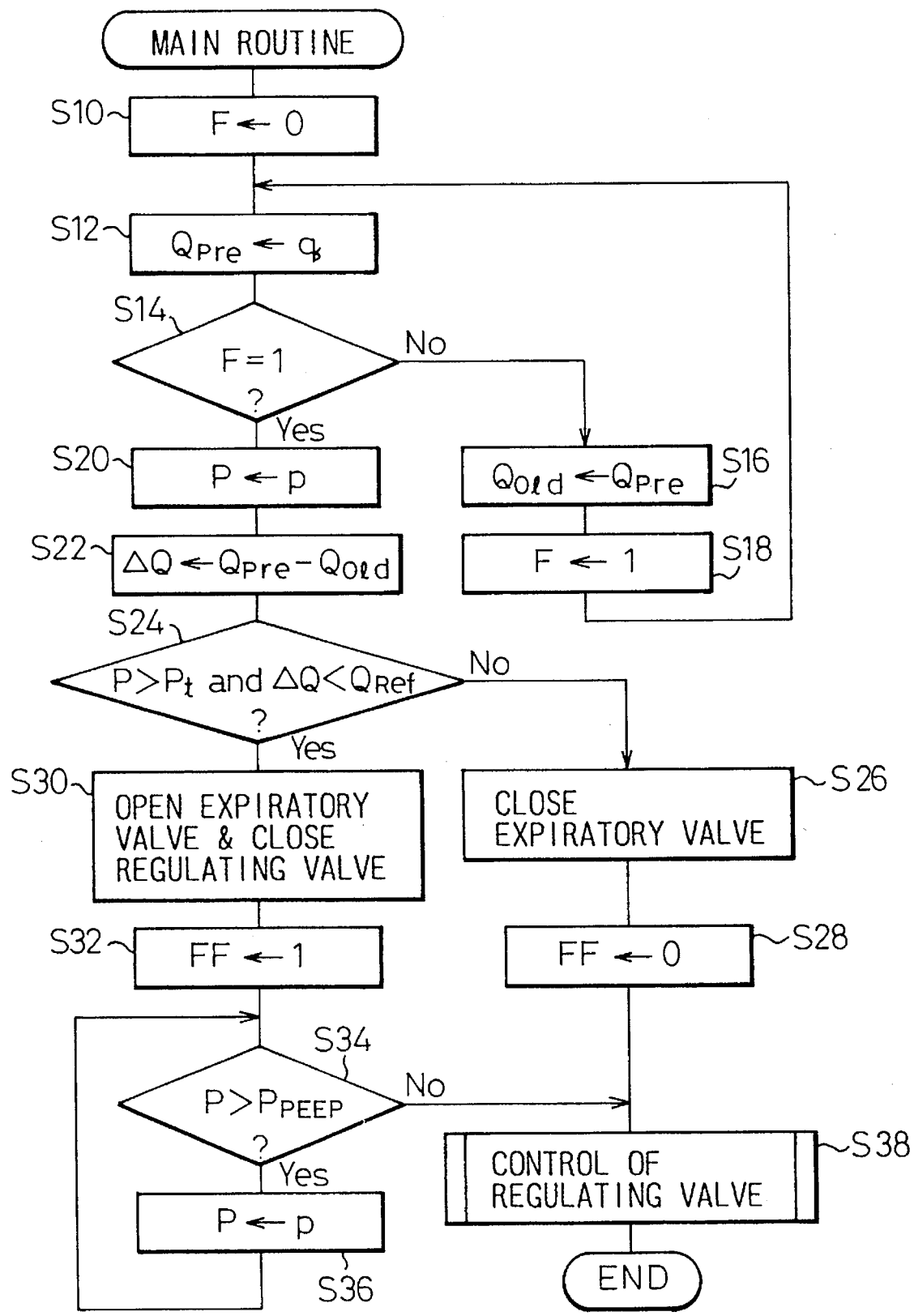
FIG. 2 is a flow chart for determining the respiratory phase in the apparatus of FIG. 1.
Figure 3:
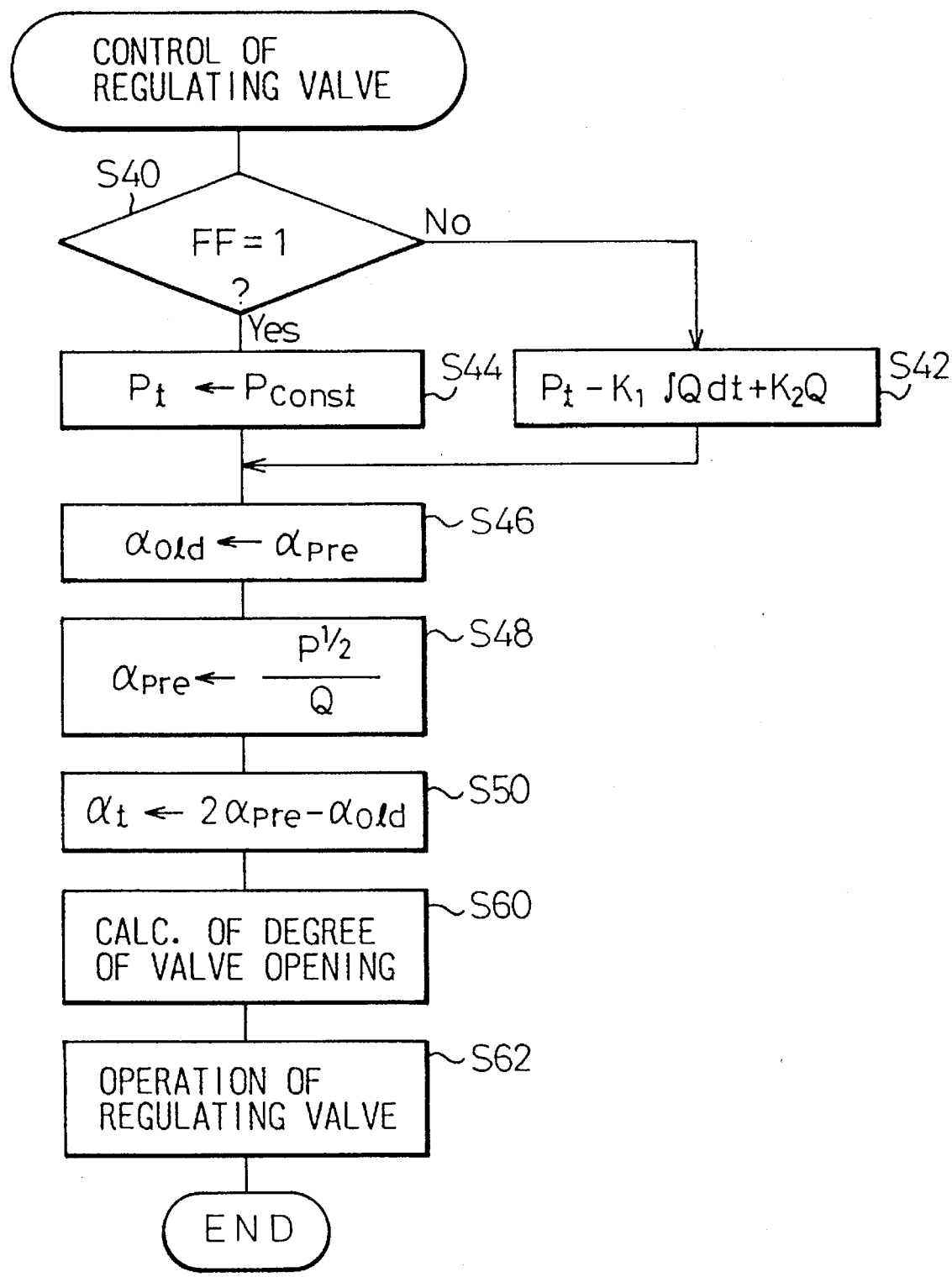
FIG. 3 is a flow chart for controlling the degree of the opening the pressure regulating valve.

With reference to FIGS. 2 and 3, the functional operation of the device for ventilating the lungs of a patient of FIG. 1 will be described. FIG. 2 illustrates a routine for determining whether the respiration of the patient is in the expiration phase or in the inspiration phase. FIG. 3 illustrates a routine for controlling the degree of the opening of the pressure regulating valve 16.

When the operation of the device is started by the patient, doctor, therapist or other operator, the routine for determining the respiration phase goes to step S10 in which zero is input to flag F. Then, in step S12, the flow rate of the respiratory gas is detected by the flow meter 18, and read into $Q_{pre}$ as the present value of the flow rate. In step S14, if F=1, the routine goes to step S20, and if F≠1, the routine goes to step S16.

In step S16, the present flow rate $Q_{Pre}$ is input into $Q_{Old}$ as the old value of the flow rate. In step S18, one is input into the flag F. Then, the routine goes to step S12. In step S12, the flow rate is read into $Q_{pre}$ again. In step S20, the pressure of the respiratory gas adjacent to the respiratory gas mask 14 is detected by the pressure sensor 20, and read into P as the present value of the pressure. In step S22, the differential value of the flow rate $\Delta Q$ is calculated by subtracting the old value the flow rate $Q_{Old}$ from the present value $Q_{pre}$.

In step S24, it is determined whether the respiration is in the inspiration phase or in the expiration phase. In this step, the present value of the pressure P is compared with a target pressure $P_t$, which is described hereinafter, and the differential flow rate $\Delta Q$ is compared with a predetermined reference value $Q_{Ref}$. The target pressure $P_t$ is a value to which the pressure regulating valve 16 regulates the pressure of the respiratory gas within the conduit 12 adjacent to the breathing mask 14. The target pressure $P_t$ can be obtained by the following equation.

$$P_t = K_1 \int Q\, dt + K_2 Q \qquad (1)$$

where $K_1$: a gain factor applied to the volume $\int Q\, dt$: the lungs volume at the present time $K_2$: a gain factor applied to the flow rate $Q$: the present flow rate The above equation is well known by those skilled in the art and is described in European Patent Publication No. 0,452,001 A2 which is incorporated herein by reference. The target pressure $P_t$ can be a predetermined constant pressure as is described in Japanese Unexamined Patent Publication (Kokai) No. 3-222963.

At first, the target pressure $P_t$ is not determined. Therefore, an appropriate value, for example the positive end-expiratory pressure (PEEP) may be input into $P_t$ initially. PEEP may be a pressure level within the range 1–20 cmH$_2$O depending of the patient to be assisted by the device.

P>$P_t$ means that the respiratory gas is supplied while the patient does not want to inspire. However, in spite of P>P$_1$, if the differential value of the flow rate $\Delta Q$ is equal to or higher than the predetermined reference value $Q_{Ref}$, that is $\Delta Q \geq Q_{Ref}$, it can be determined that the patient is still inspiring. Thus, in this case, it is determined that the respiration is in the inspiration phase. On the other hand, P$\leq$P$_t$ means that a volume of the respiratory gas equal to the volume required by the patient is supplied, or that insufficient respiratory gas is supplied. Therefore, in this case, it can be determined that the respiration is in the inspiration phase.

In step S24, if P>$P_t$ and $\Delta Q<Q_{Ref}$, it is determined that the respiration is in the expiration phase and the routine goes to step S30. If not, it is determined that the respiration is in the inspiration phase and the routine goes to step S26.

When the respiration is in the inspiration phase, the routine goes to step S26. In step S26, the main expiratory valve 22 is closed to supply the respiratory gas to the patient efficiently. In step S28, zero is input into flag FF to indicate the inspiration phase. Then, the routine goes to step S38 to jump to a subroutine for controlling the pressure regulating valve 16 which is shown in FIG. 3.

When the respiration is in the expiration phase, the routine goes to step S30. In step S30, the main expiratory valve 22 is opened to reduce the pressure within the conduit 12 effectively. That is, the solenoid 24a of the solenoid operated shut-off valve 24 is energized by the solenoid driver 40 which results in the fluid communication between the conduit 12 upstream of the pressure regulating valve 16 and the piston 22a of the main expiratory valve 22. Thus, the main expiratory valve 22 opens to reduce the pressure within the conduit 12 rapidly and effectively.

At the same time, in step S30, the pressure regulating valve 16 is completely closed to separate the respiratory gas mask 14 from the fan 10. Thus, the expiratory gas from the patient is exhausted through the main expiratory valve 22. In step S32, one is input into the flag FF to indicate the expiration phase.

In step S34, it is determined whether the pressure P is higher than PEEP. If so, the routine goes to step S36 in which the present pressure within the conduit 12 is read agin, and returns to step S34. If the pressure is lower than or equal to PEEP, the routine goes to step S38.

In order to assist in ventilating the lungs of a patient, in particular, in case of a patient who has sleep apnea syndrome, the device must keep the minimum pressure equal to or higher than PEEP (the minimum pressure can be higher than PEEP by a pressure, for example 0.5–1.5 cmH$_2$O). On the other hand, during the expiration phase, in order to exhaust the expiratory gas from the conduit through the main expiratory valve 22 rapidly, it is necessary to keep the main expiratory valve 22 open and the pressure regulating valve 16 closed. Thus, the controller 26 monitors the pressure within the conduit 12 continuously in steps S34 and S36.

When the pressure is reduced to a pressure level equal to or lower than PEEP, the routine goes to step S38 to jump to the subroutine for controlling the pressure regulating valve 16.

The above mentioned routine for determining the respiration phase is executed at a time interval, preferably, within the time range of 20–50 msec and, most preferably, of 30 msec.

With reference to FIG. 3, the subroutine for controlling the degree of the opening of the pressure regulating valve 16 to regulate the pressure to the target pressure is described.

In step S40, if FF=1, that is in case of the expiration phase, the routine goes to step S44. In step S40, in case of the inspiration phase, the routine goes to step S42. In step S42, the target pressure P$_t$ is calculated by the above-mentioned equation (1). In step S44, a predetermined constant target pressure P$_{Const}$, which may preferably correspond to PEEP, is input into P$_t$.

Then, the routine goes to step S46 in which a parameter $\alpha_{Pre}$ is input into a parameter $\alpha_{Old}$. The parameter $\alpha$ is defined, in this embodiment, as follows.

$$\alpha = \frac{P^{1/2}}{Q} \quad (2)$$

From Berunoulli's theorem, we obtain the following equation.

$$\frac{1}{2}\rho v^2 + \frac{P}{\rho} = \text{const.} \quad (3)$$

The flow rate is represented by the following equation.

$$Q = A \, v \quad (4)$$

where
A: the sectional area of the conduit

From the equations (3) and (4), we obtain the following equation.

$$\frac{1}{2}\rho \left\{ \frac{Q}{A} \right\}^2 + \frac{P}{\rho} = \text{const.} \quad (5)$$

The equation (5) means that there is a direct relationship between the square of the flow rate and the pressure. Therefore, we introduce the parameter $\alpha$ as a parameter which represents the ratio of potential of the flow system relative to the flow rate, that is a resistance or an impedance in a flow system.

The flow resistance parameter also can be defined as following equation.

$$\alpha' = \frac{P}{Q^2} \quad (6)$$

Further, the flow resistance parameter may be defined as following equation within a limited flow condition as long as the parameter can appropriately represent the flow impedance.

$$\alpha'' = \frac{P}{Q} \quad (7)$$

Further, the flow impedance parameter can be defined by a equation which includes at least one term selected from $\alpha$, $\alpha'$ and $\alpha''$.

In step S48, the present value of the parameter $\alpha_{Pre}$ is calculated. In step S50, a predicted value of the parameter $\alpha_P$ is calculated by the first order extrapolation based on the preceding value of the parameter and the present value of the parameter as shown by the following equation.

$$\alpha_P = 2\alpha_{Pre} - \alpha_{Old} \quad (8)$$

The predicted parameter $\alpha_P$ represents the flow resistance or flow impedance of the flow system downstream of the pressure sensor 20 including the airway, the resilience of the lungs of the patient and etc. to which value, the parameter $\alpha$ may vary after the next time interval.

Figure 5:
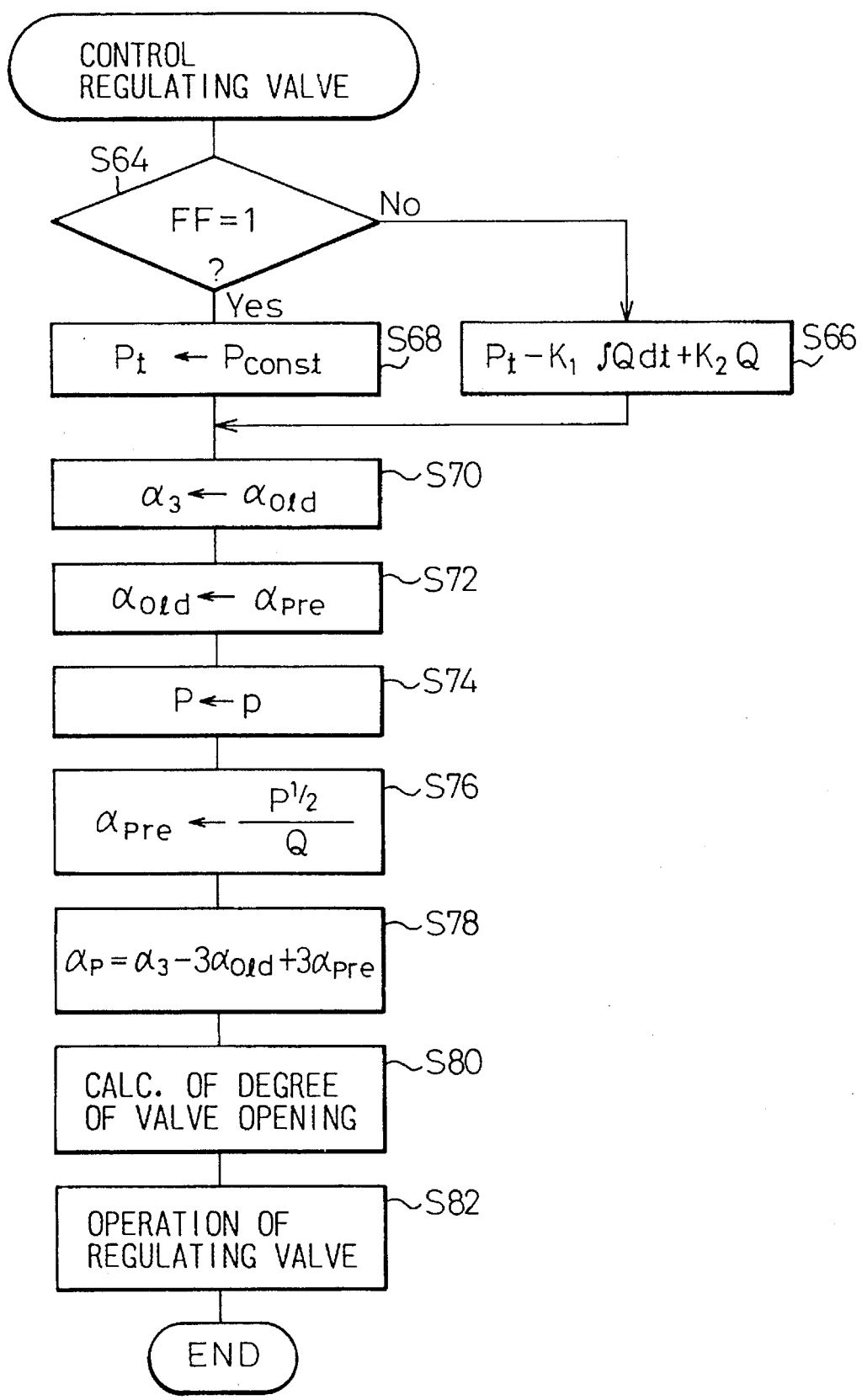
FIG. 5 is another flow chart for controlling the degree of the opening the pressure regulating valve, in which the predicted flow resistance parameter is calculated by a second order extrapolation.

In this embodiment, the predicted parameter $\alpha_P$ is calculated by the first order extrapolation. However, as shown in FIG. 5, the predicted parameter $\alpha_P$ can be obtained by the second order extrapolation as follows. That is, the second preceding parameter $\alpha_{Old}$ is input into $\alpha_3$ in step S70. The preceding value of the parameter $\alpha_{Pre}$ is input into $\alpha_{Old}$ in step S72. The present value of the pressure is read into P in step S74. The present value of the parameter is calculated in step S76. The predicted parameter is calculated by the following equation in step S78.

$$\alpha_P = \alpha_3 - 3\alpha_{Old} + 3\alpha_{Pre} \quad (9)$$

Further, it can be determined by a higher order equation.

Then, the routine goes to step S60 in which the degree of the opening of the pressure regulating valve 16 is determined by using the predicted parameter $\alpha_P$ such that the pressure within the conduit 12 at the next time interval, for example after 30 msec, is suitable for the respiration, which is predicted by the parameter $\alpha_P$ as follows.

Figure 4:
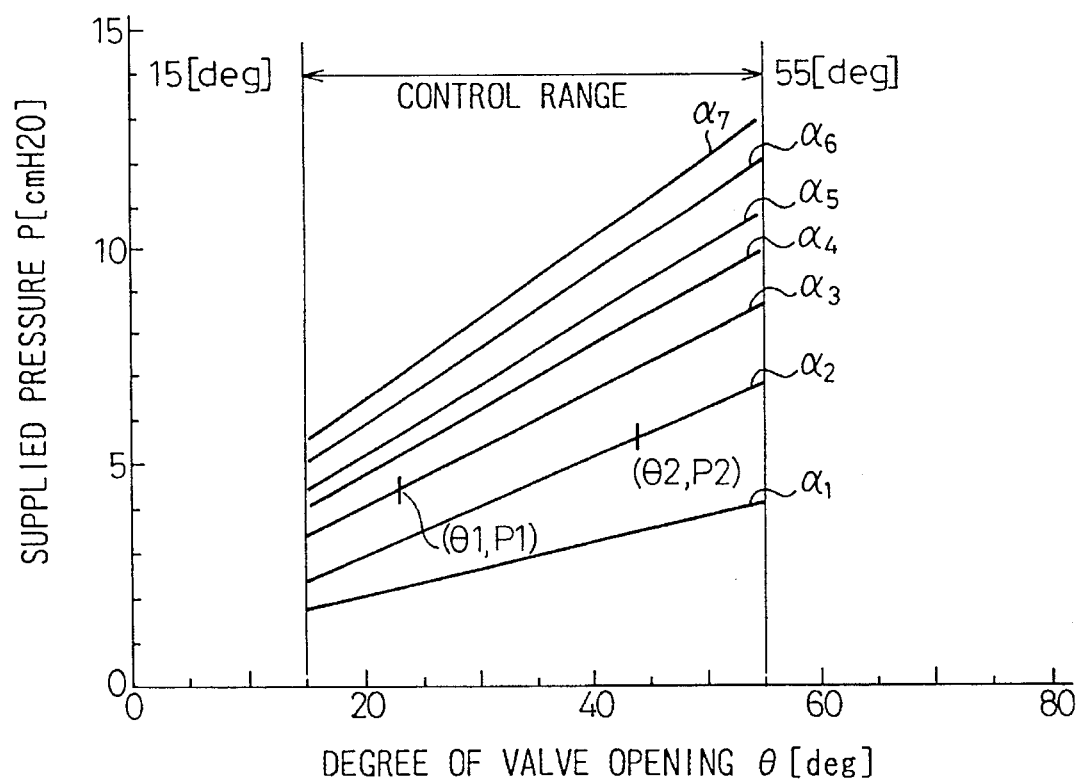
FIG. 4 illustrates experimental data of the pressure of the respiratory gas within the respiratory gas conduit relative to the degree of the opening of the pressure regulating valve for various values of the flow resistance parameter.

With reference to FIG. 4, the method of determining the degree of the opening of the pressure regulating valve 16 will be described.

FIG. 4 illustrates the pressure P within the conduit 12 relative to the degree $\theta$ of the opening of a pressure regulating valve, which was experimentally obtained by varying the value of the parameter $\alpha$.

The experiment was carried out by a experimental apparatus which comprises a air source, an air conduit, a pressure regulating valve on the air conduit, a sensor for detecting the degree of the opening of the pressure regulating valve, a flow meter on the air conduit downstream of the pressure regulating valve, a pressure sensor on the air conduit downstream of the flow meter, and a variable orifice on the air conduit downstream of the pressure sensor.

As mentioned above, the parameter $\alpha$ represents the flow resistance or flow impedance of a flow system downstream of the pressure sensor, and does not depend on the constitution of the flow system but only on the flow resistance. Therefore it can be determined by only the flow resistance. This means that the experimental data can be used for determine the degree of the opening of the pressure regulating valve of an actual device for assisting in ventilating the lungs of a patient, if the pressure regulating valve of the actual device is the same as the experimental apparatus. In the illustration of FIG. 4, when the present value of the parameter is $\alpha_3$ and the present pressure is $P_1$, it is determined that the degree of the opening of the pressure regulating valve is about 22 degree ($\theta_1=22$). From this condition, if it is predicted that the parameter will change to $\alpha_2$, and the target pressure is calculated $P_2$, the degree of the opening of the pressure regulating valve is determined about 43 degree ($\theta_2=43$).

In this embodiment of the invention, the experimental data is stored in the ROM 30 of the controller 26 in the form of linear equations. However, the experimental data can be stored in the ROM 30 in the form of a data table.

From step S60, the routine goes to step S62 in which the motor operated valve 16 is controlled its degree of opening.

From the above mentioned description, it will be understood that, in the invention, the degree of the opening of the pressure regulating valve is controlled so that the pressure within the air conduit adjacent to the breathing mask becomes the target pressure based on prediction and not on feed-back control.

With reference to FIG. 5, the second embodiment will be described.

FIG. 5 illustrates a routine for controlling the motor operated butterfly valve 16 to regulate the pressure according to the second embodiment of the invention. This routine is the same as one in FIG. 3 except for step S78. In the first embodiment, the predicted parameter $\alpha_P$ is calculated by the first order extrapolation. However, in this embodiment, the predicted parameter $\alpha_P$ can be obtained by the second order extrapolation as shown in step S78.

Figure 6:
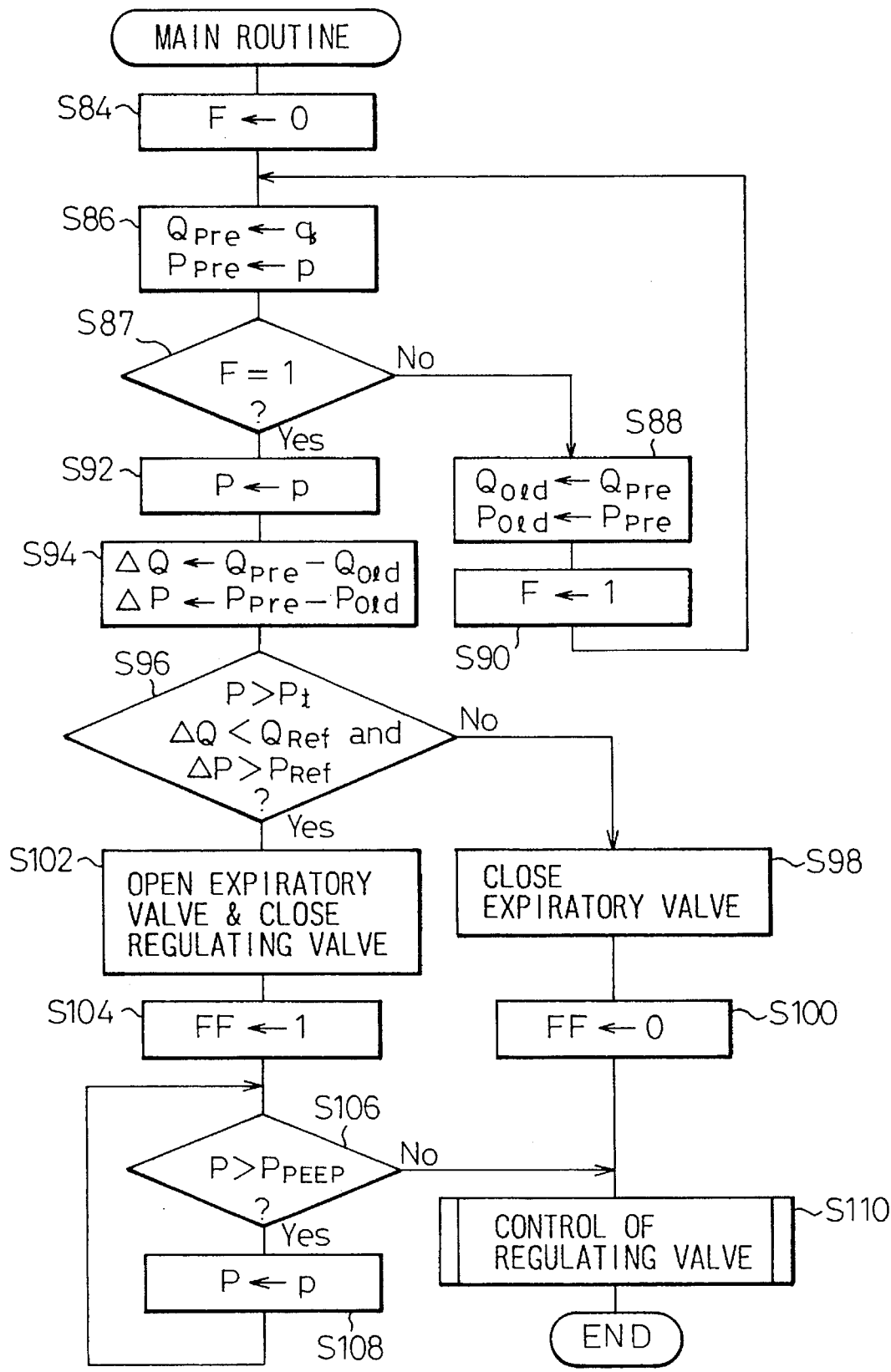
FIG. 6 is another flow chart for determining the respiratory phase.

With reference to FIG. 6, the third embodiment of the invention will be described. In the third embodiment, the respiration phase is determined by the present pressure adjacent to the respiratory gas mask 14, the differential value of the flow rate of the respiratory gas, and the differential value of the pressure while it is determined by the present pressure, and the differential value of the flow rate, in the embodiment described with reference to FIG. 2.

When the operation of the device is started by the patient, doctor, therapist or other operator, the routine for determining the phase of the respiration shown in FIG. 6 goes to step S84 in which zero is input to flag F. Then, in step S86, the present value of the flow rate and the pressure are read into $Q_{pre}$ and $P_{pre}$ by the flow meter 18 and the pressure sensor 20. In step S87, if F=1, the routine goes to step S92, and if F≠1, the routine goes to step S88.

In step S88, the present value of the flow rate $Q_{Pre}$ is input into $Q_{Old}$, and the present value of the pressure $P_{Pre}$ is input into $P_{Old}$. In step S90, one is input into the flag F. Then, the routine goes to step S86. In step S86, the flow rate and the pressure are read into $Q_{pre}$ and $P_{pre}$ again. In step S92, the present value of the pressure $P_{pre}$ is input into P.

In step S94, the differential value of the flow rate $\Delta Q$ and the pressure $\Delta P$ are calculated by subtracting the old value of the flow rate and of the pressure $Q_{Old}$ and $P_{Old}$ from the present value $Q_{pre}$ and $P_{pre}$ respectively.

In step S96, the respiration phase is determined. In this step, the present pressure P is compared with the target pressure $P_t$, the differential flow rate $\Delta Q$ is compared with a predetermined reference flow rate $Q_{Ref}$ as in the preceding embodiments. In this embodiment, further the differential pressure $\Delta P$ is compared with a reference differential pressure $\Delta P_{Ref}$. The other steps are the same as those of the flow chart shown in FIG. 2.

By adding the comparison of the differential pressure $\Delta P$ for determing the respiration phase, finer control of the pressure regulation can be obtained compared with the preceding embodiments.

Figure 7:
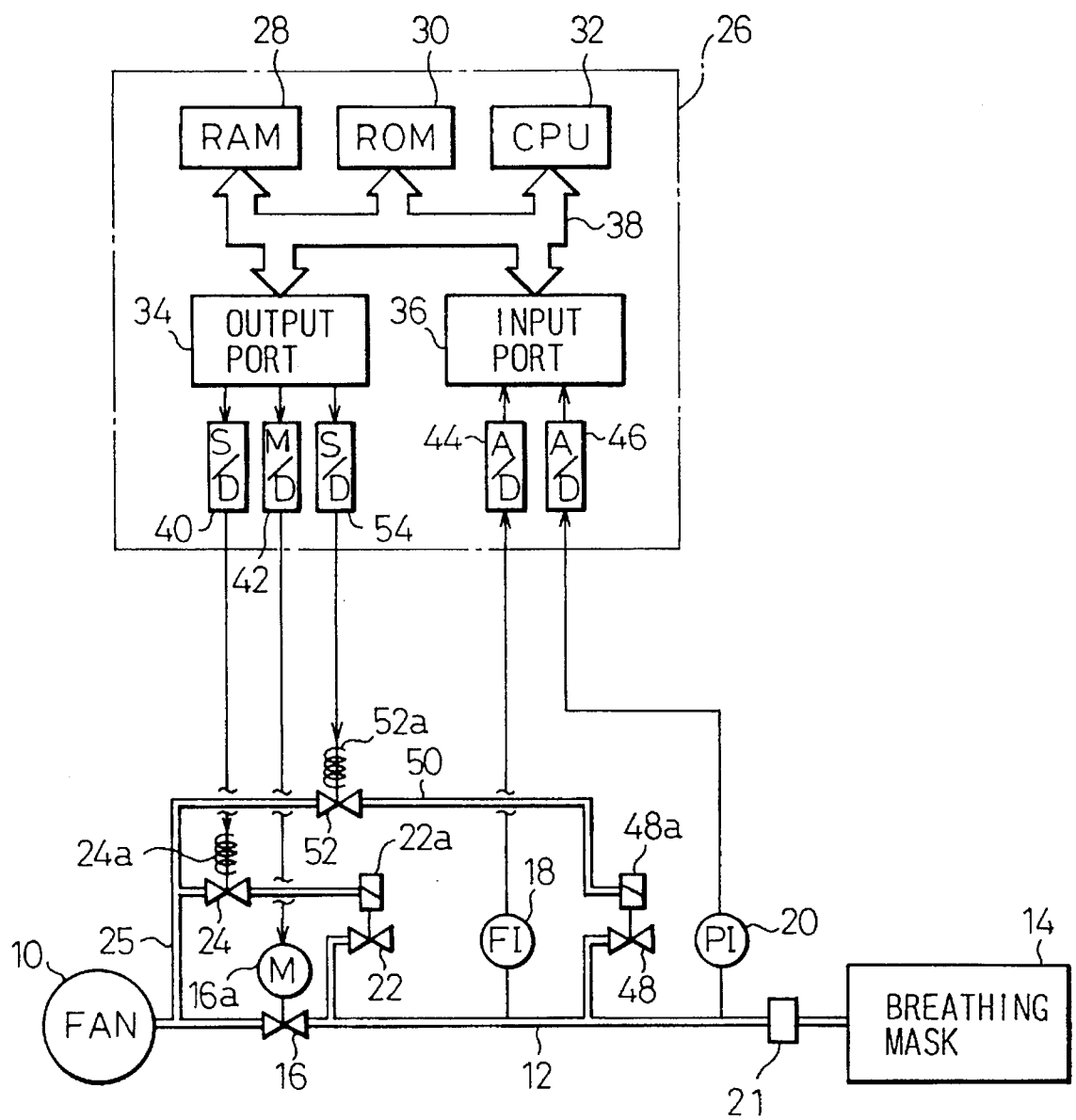
FIG. 7 is a schematic of an apparatus for ventilating the lungs of a patient according to another embodiment of the invention in which an additional expiratory valve is provided in the respiratory gas conduit.

In FIG. 7, elements identical to those in FIG. 1 are indicated by the same reference numbers. With reference to FIG. 7, another embodiment will be described. In this embodiment, the device for assisting in ventilating the lungs of a patient further comprises an additional expiratory valve, such as a piston operated shut-off valve 48 on the conduit 12 downstream of the flow meter 18 and upstream of the pressure sensor 20. The piston operated shut-off valve 48 has a piston 48a for operating the shut-off valve 48 between open and closed position. The piston 48a is connected to the conduit 12 upstream of the pressure regulating valve 16 through a second branch conduit 50 and a first branch conduit 25. The pressure within the conduit 12 is more effectively reduced when the piston operated shut-off valves 22 and 48 are open compared with the embodiment of FIG. 1.

A solenoid operated shut-off valve 52 is provided in the second branch conduit 50 between the first branch conduit 25 and the piston 48a. The solenoid operated shut-off valve 52 has a solenoid 52a which is electrically connected to the control unit 26. The solenoid operated valve 52 can operatively move between open and closed positions. When the solenoid 52a is energized, the solenoid operated shut-off valve 52 moves to the open position where the pressure within the conduit 12 upstream of the pressure regulating valve 16 is applied to the piston 52a to open the piston operated shut-off valve 48. When the solenoid 52a is deenergized, the solenoid operated shut-off valve 52 moves to the closed position where the piston 52a is separated from the conduit 12.

The control unit 26 comprises a random access memory (RAM) 28, a read only memory (ROM) 30, a central processing unit (CPU) 32, an output port 34, and an input port 36 which are connected to each other by a bidirectional bus 38. The solenoids 24a and 52a are connected to the output port 34 through solenoid drivers 40 and 54.

The other constitutions of the device according to this embodiment is the same as the preceding embodiment of FIG. 1. Therefore, further descriptions regarding the constitutions are omitted.

Figure 8:
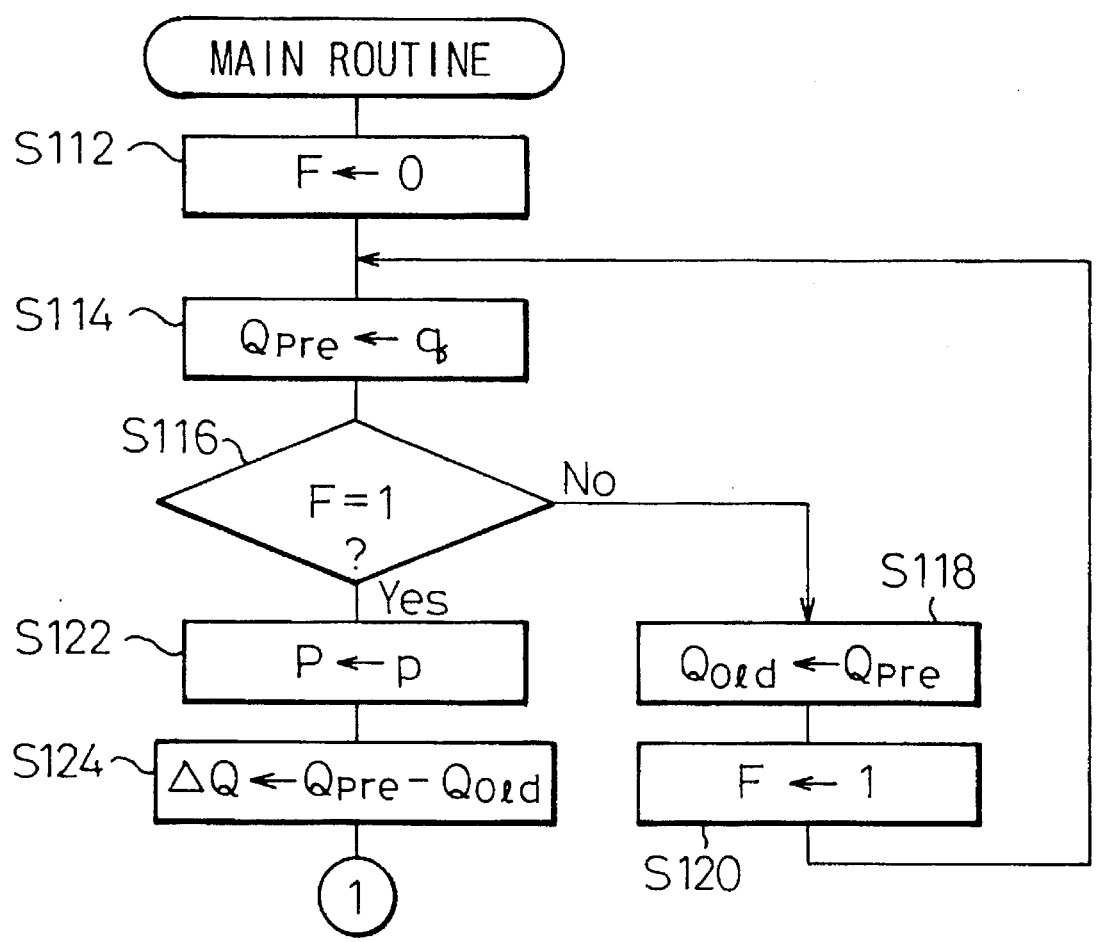
FIGS. 8 and 9 are parts of a flow chart for determining the respiratory phase in the apparatus of FIG. 7.
Figure 9:
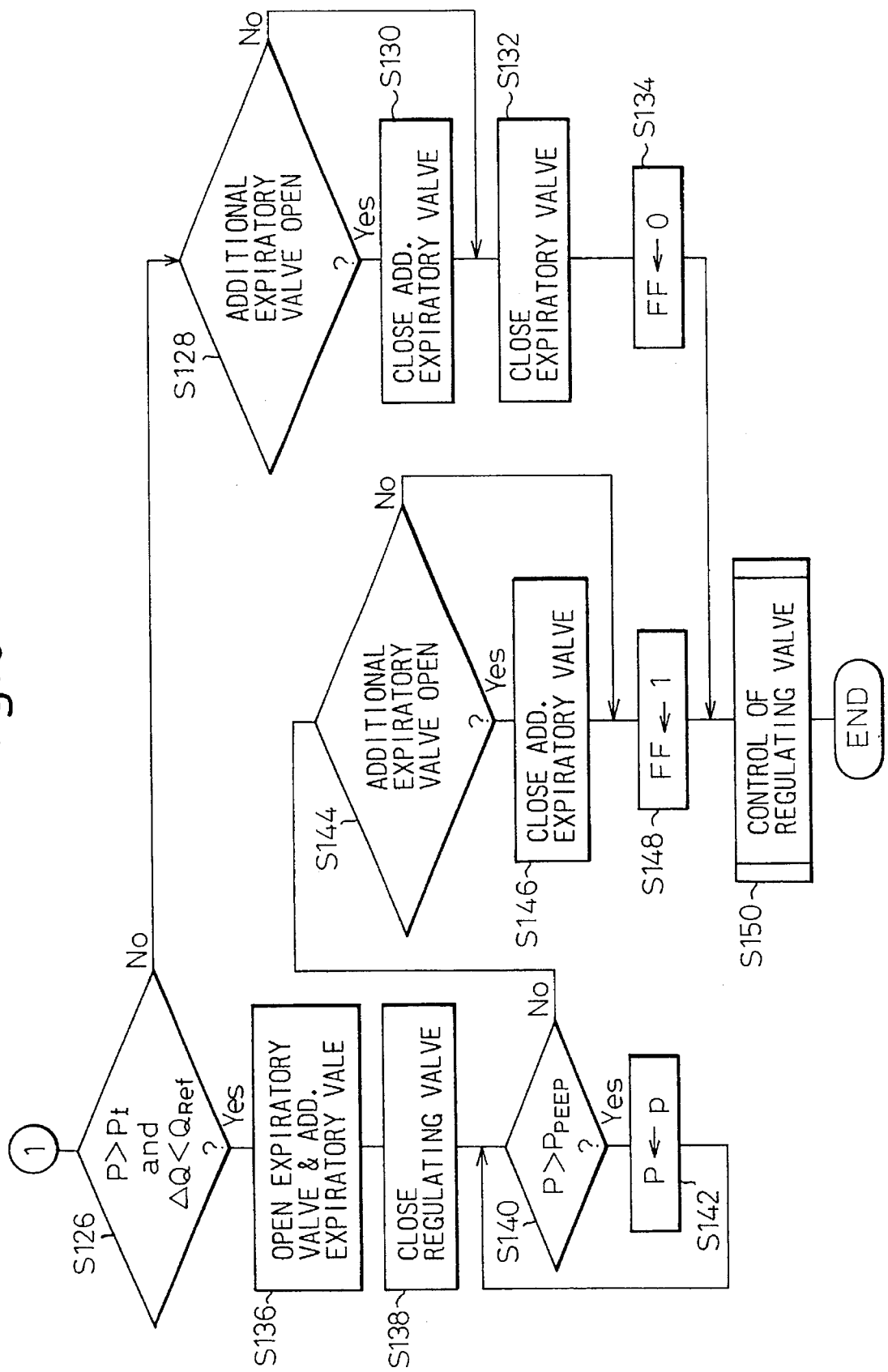

With reference to FIGS. 8 and 9, the functional operation of the device for assisting in ventilating the lungs of a patient according to this embodiment will be described. FIGS. 8 and 9 illustrate a routine for determining the respiration phase and operating the main expiratory valve 22 and the additional expiratory valve 48. Steps S112 through S126 are the same as the steps S10 through S24 shown in FIG. 2.

When the routine goes to step S126, it is determined whether the respiration is in the expiration phase or in the inspiration phase by the present pressure adjacent to the respiratory gas mask and the differential flow rate of the respiratory gas as in the embodiment of FIG. 1.

When the respiration is in the inspiration phase, the routine goes to step S128 in which it is determined whether the additional expiratory valve 48 is open. If not, the routine goes to step S132 to close the main expiratory valve 22. If the additional expiratory valve 48 is open, it is closed in step S130. That is, the solenoid 52a of the solenoid operated shut-off valve 52 is deenergized which results in separating the piston 48a of the additional expiratory valve 48 from the conduit 12. Thus, the additional expiratory valve 48 is closed.

In step S132, the main expiratory valve 22 is closed to supply the respiratory gas to the patient efficiently. In step S134, zero is input into flag FF to indicate the inspiration phase. Then, the routine goes to the routine for controlling the pressure regulating valve 16 in step S150. The routine for controlling the pressure regulating valve 16 was already described.

In step S126, if the respiration is in the expiration phase, the routine goes to step S136 in which the main expiratory valve 22 and the additional expiratory valve 48 are opened to reduce the pressure within the conduit 12 effectively. That is, the solenoids 24a and 52a of the solenoid operated shut-off valves 24 and 52 are energized by the solenoid drivers 40 and 54 which results in fluid communication between the conduit 12 upstream of the pressure regulating valve 16 and the pistons 22a and 52a of the main expiratory valve 22 and the additional expiratory valve 52. Thus, the main expiratory valve 22 and the additional expiratory valve 52 are opened to reduce the pressure within the conduit 12 rapidly and effectively.

In step S138, the pressure regulating valve 16 is completely closed to separate the respiratory gas mask 14 from the fan 10. Thus, the expiratory gas from the patient is exhausted through the main expiratory valve 22 and the additional expiratory valve 48. In particular, providing the additional expiratory valve 48 on the conduit 12 adjacent to the respiratory gas mask 14 allows the expiratory gas from the patient to be exhaust directly, which results in substantially no reverse flow of the expiratory gas through the conduit 12. Therefore, there is substantially no expiratory gas remaining within the conduit 12, which is particularly advantageous in case of low PEEP.

A lower PEEP makes the pressure regulating valve close during the longer time, since the step 106 keeps the routine waiting until the pressure is reduced to PEEP, during which the expiratory gas from the patient reversely flows to the main expiratory valve 22. Therefore, the conduit 12 is filled with the expiratory gas which includes carbon dioxide. When the pressure becomes lower than or equal to PEEP, the the pressure regulating valve is controlled to regulate the pressure at PEEP in step S32 or S110 which allows the respiratory gas to flow to downstream. The lower PEEP allows the lower flow rate. Therefore, the expiratory gas within the conduit 12 cannot be exhausted sufficiently through the expiratory port 21. When the respiration changes from the expiration phase to the inspiration phase, the patient inspires the remaining expiratory gas within the conduit again, which results in oxygen deficit of the patient. The additional expiratory valve can reduce the reverse flow of the expiratory gas to the main expiratory valve 22.

In step S140 it is determined whether the pressure P is higher than PEEP. If so, the routine goes to step S142 in which the present pressure within the conduit 12 is read agin, and returns to step S140. If the pressure is lower than or equal to PEEP, the routine goes to step S144.

In step S144, it is determined whether the additional expiratory valve 48 is open. If not, the routine goes to step S148. If the additional expiratory valve 48 is open, it is closed in step S146.

That is, the solenoid 52a of the solenoid operated shut-off valve 52 is deenergized which results in separating the piston 48a of the additional expiratory valve 48 from the conduit 12. Thus, the additional expiratory valve 48 is closed.

In step S148, one is input into flag FF to indicate the expiration phase. Then, the routine goes to the routine for controlling the pressure regulating valve 16 in step S150. The routine for controlling the pressure regulating valve 16 was already described.

Figure 10:
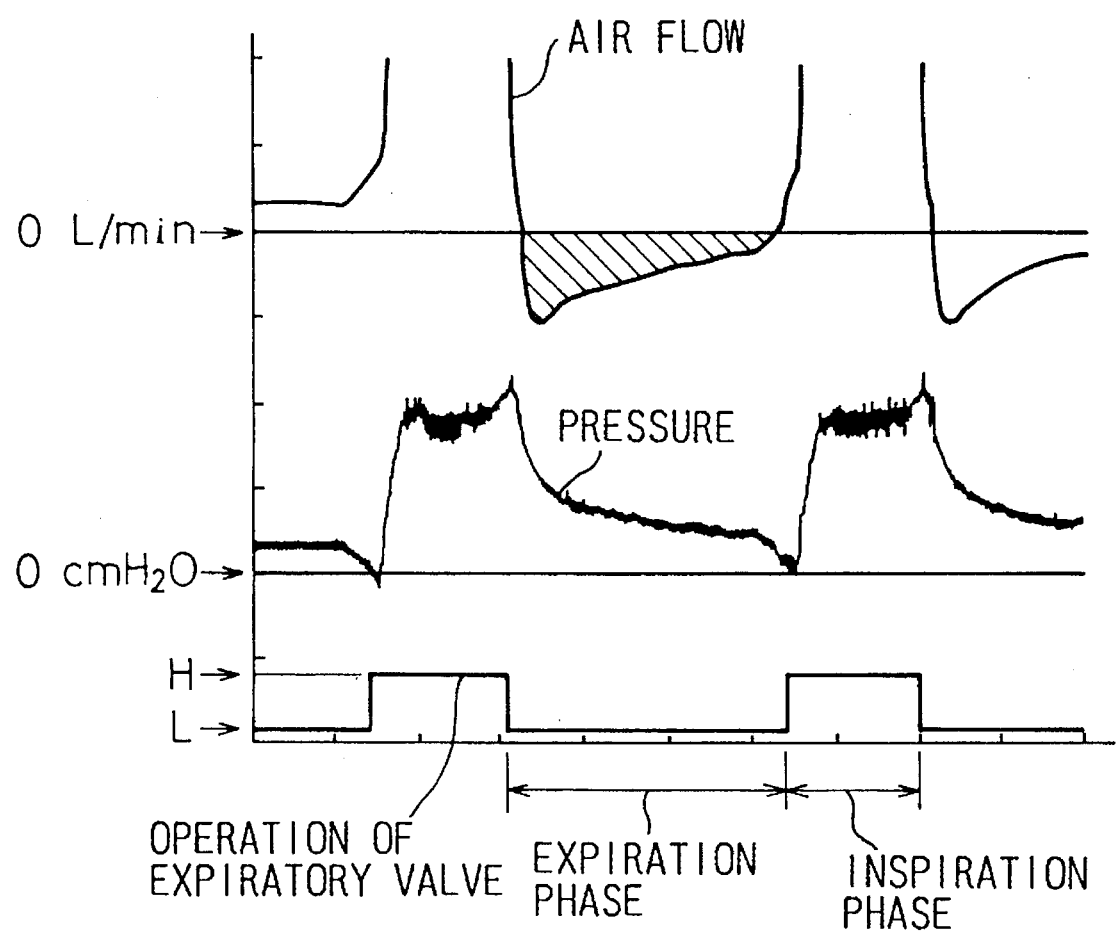
FIG. 10 illustrates the variation of the pressure and the flow rate of the respiratory gas during one respiratory cycle assisted by the apparatus of FIG. 1.
Figure 11:
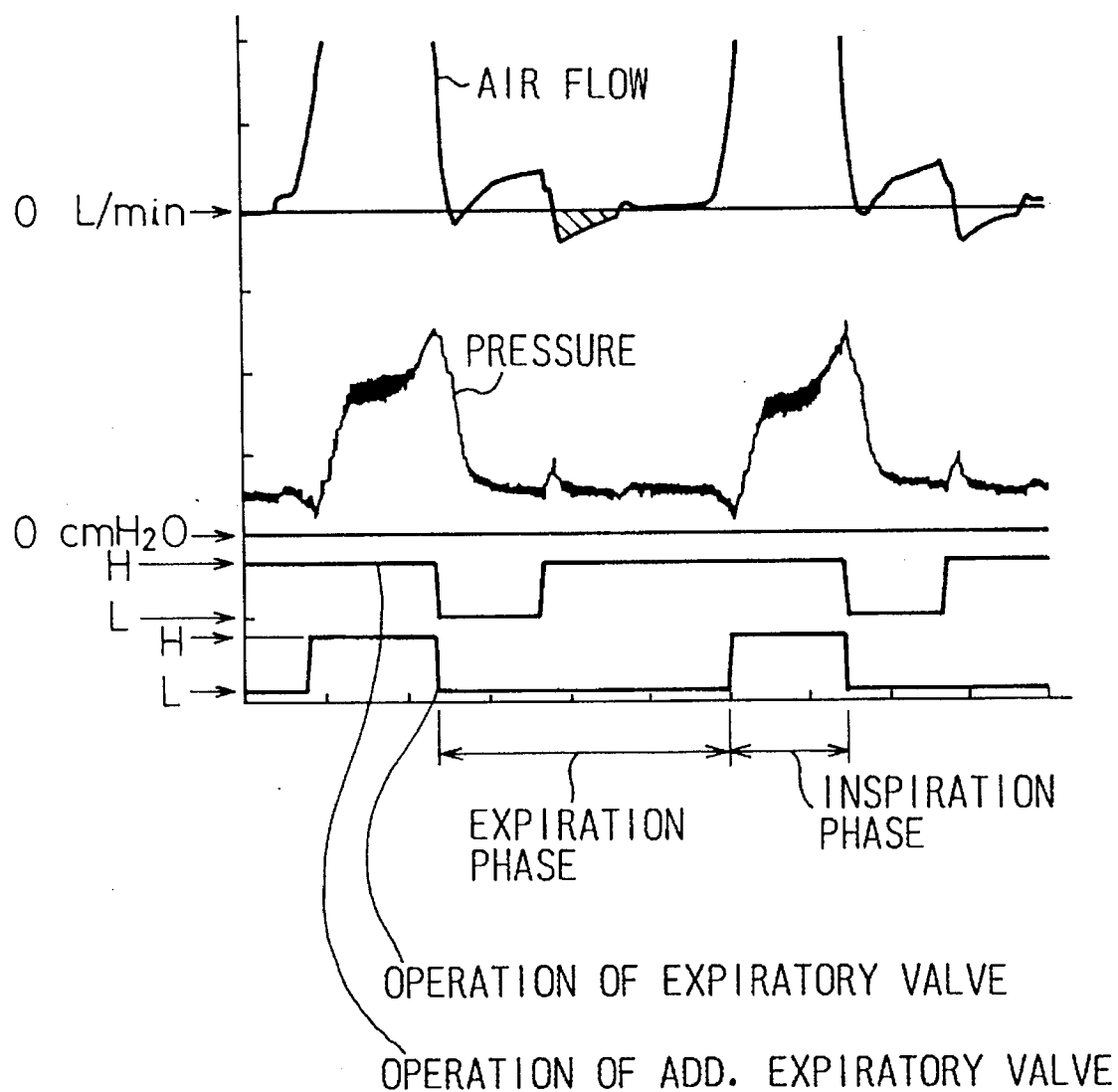
FIG. 11 illustrates the variation of the pressure and the flow rate of the respiratory gas during one respiratory cycle assisted by the apparatus of FIG. 7.

FIGS. 10 and 11 illustrate the variations in the pressure and the flow rate of the respiratory gas during one cycle of a respiration assisted by the inventive device with only the main expiratory valve (FIG. 10) and both the main and additional expiratory valves (FIG. 11). In FIGS. 10 and 11, the high signal (H) indicates that the main expiratory valve and the additional expiratory valve open, and the low signal (L) indicates that the main expiratory valve and the additional expiratory valve close.

In FIGS. 10 and 11, the hatched areas which are enclosed by the horizontal line of 0 L/min and the curve of the air flow under the 0 L/min line show the volume of reverse flow of expiratory gas from the breathing mask toward the pressure regulating valve. Comparing FIGS. 10 and 11, it will be understood that the hatched area of FIG. 10 is larger than that of the FIG. 11. This means that the reverse flow is reduced by providing the additional expiratory valve.

Figure 12:
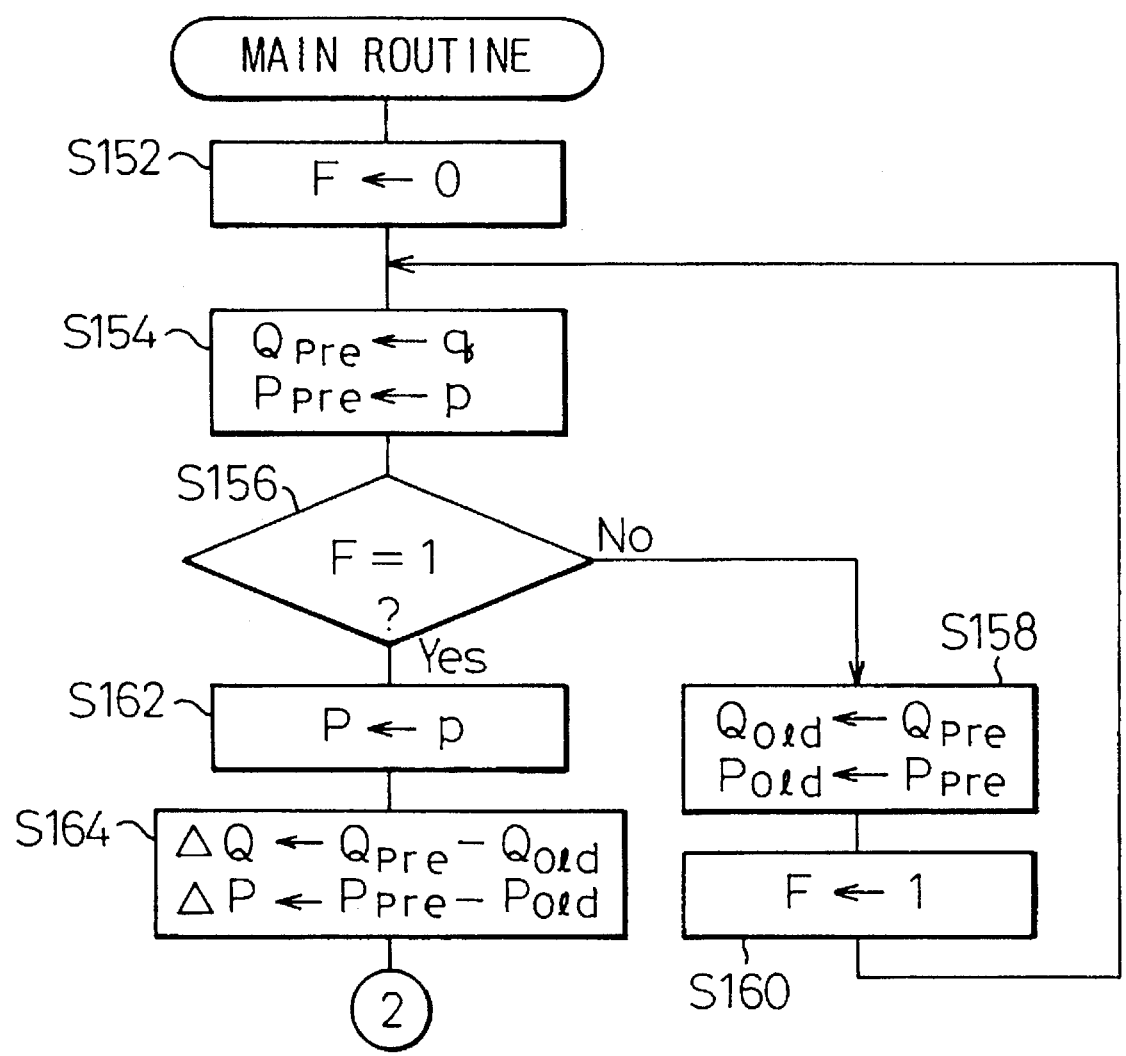
FIGS. 12 and 13 are parts of another flow chart for determining the respiratory phase in the apparatus of FIG. 7.
Figure 13:
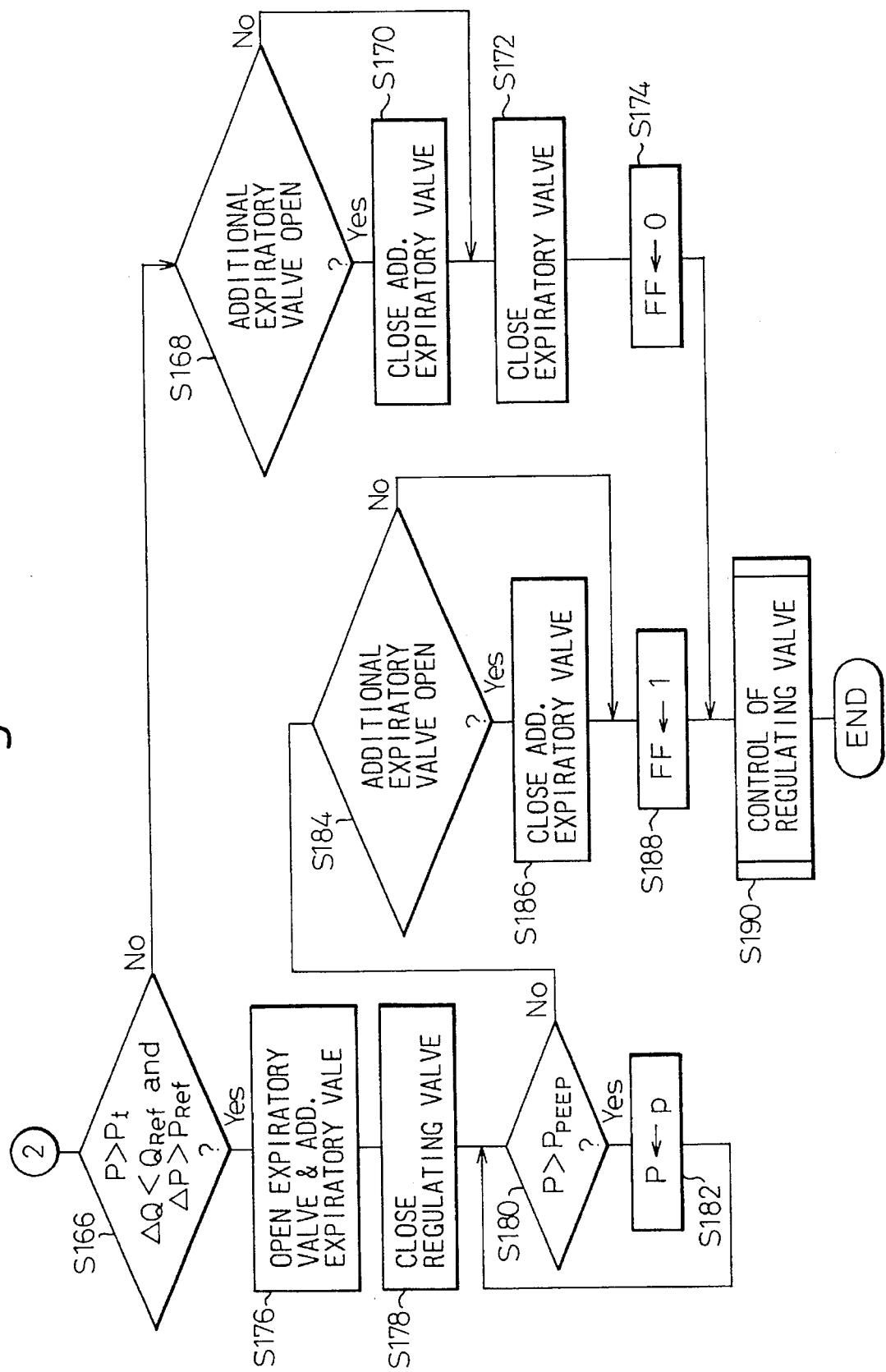

The device according to the embodiment of FIG. 7 can be also operated to determine whether the respiration is in the expiration phase by using the present pressure and the differential pressure of the respiratory gas adjacent to the breathing mask, and the differential flow rate of the respiratory gas as shown in a flow chart of FIGS. 12 and 13.

Figure 14:
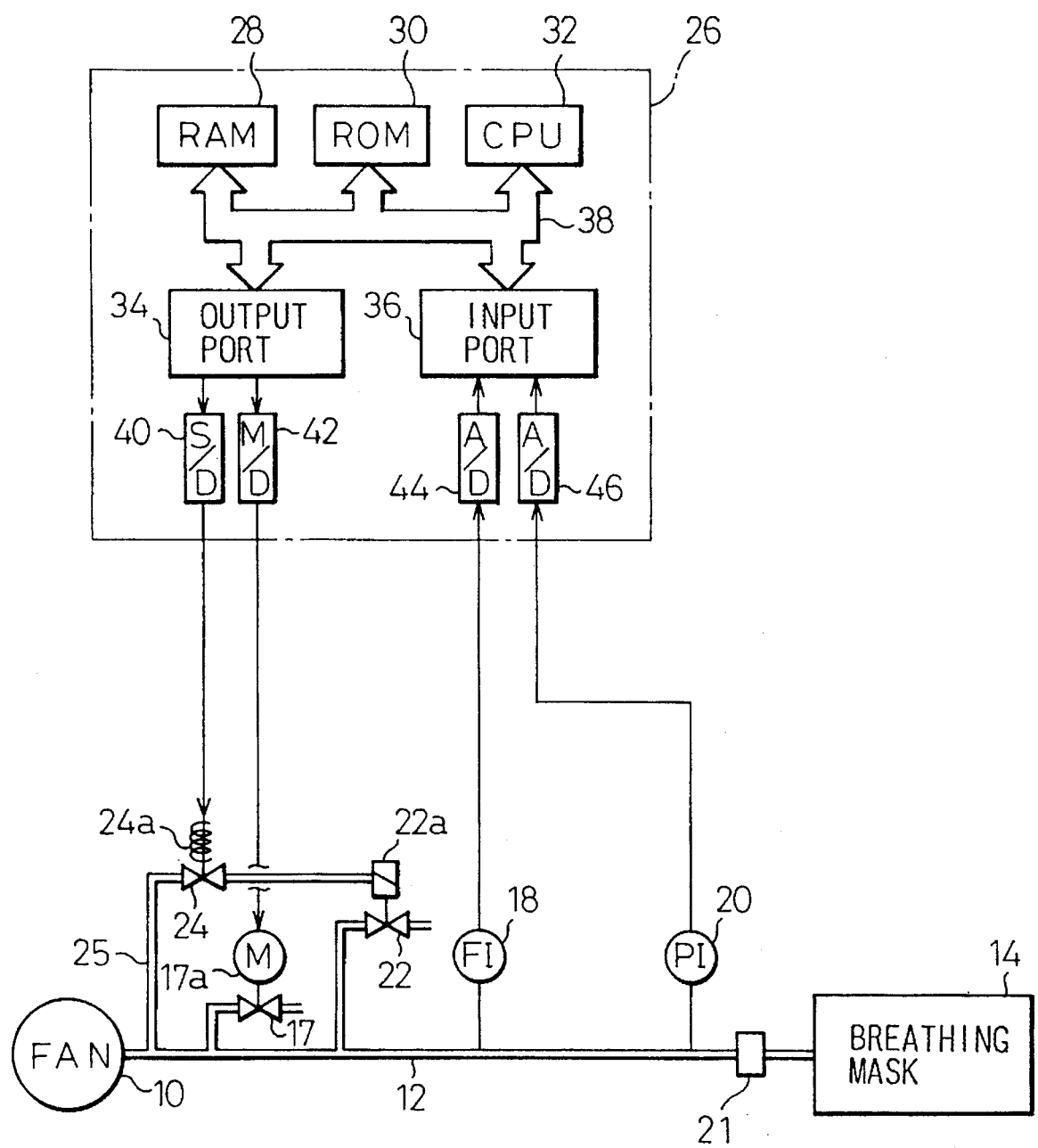
FIG. 14 is a schematic of an apparatus for ventilating the lungs of a patient according to another embodiment of the invention in which the pressure regulating valve exhausts a portion of the respiratory gas to regulate the pressure.

With reference to FIG. 14, another embodiment of the invention will be described.

In the embodiment of the FIG. 1, the pressure regulating valve, that is, the pressure regulating valve 16 has inlet and outlet ports which are connected to the discharge port of the fan 10 and the inlet port of the breathing mask 14, respectively. Therefore, substantially all the air flow from the fan passes through the pressure regulating valve 16. However, the motor operated valve 16 can regulate the pressure within the conduit 12 by exhausting the respiratory gas as shown in FIG. 14. In FIG. 14, the pressure regulating valve is a pressure regulating valve 17 with a driving motor 17a which is electrically connected to the output port 34 of the controller 26 through the motor driver 42. The pressure regulating valve 17 has an inlet port connected to the conduit 12 and an outlet port opening to the environment. Thus, the pressure regulating valve 17 regulates the pressure within the conduit 12 downstream thereof by exhausting a portion of the respiratory gas from the fan 10. The other elements, constitution and operation are the same as the preceding embodiments.

We claim:

1. An apparatus for assisting in ventilating the lungs of a patient comprising:

a respiratory gas source means for supplying the respiratory gas to a patient;

a breathing mask means for introducing the respiratory gas into the lungs of a patient, the breathing mask being suitable to be put on the face of a patient;

a conduit means for fluidly connecting the respiratory gas source means to the breathing mask for delivering the respiratory gas from the respiratory gas source means to the breathing mask;

a means for regulating the pressure within the conduit means;

a flow meter means for detecting the flow rate of the respiratory gas from the respiratory gas source to the breathing mask;

a pressure sensor means for detecting the pressure within the conduit adjacent to the breathing mask;

a means for obtaining a flow impedance parameter of the flow system downstream of the pressure sensing means, including the airways and the lungs of the patient, based on the flow rate and pressure detected by the flow meter and the pressure sensor means;

a means for storing the relationship between the operation of the pressure regulating means, the flow impedance parameter, and the pressure within the conduit means;

a means for predicting the flow impedance parameter after a predetermined time interval within a respiratory cycle;

a means for generating a target pressure signal to which the pressure regulating means regulates the pressure within the conduit; and a means for controlling the operation of the pressure regulating means such that the pressure within the conduit adjacent to the breathing mask becomes substantially the target pressure during the respiratory cycle based on the predicted flow impedance parameter and the relationship between the operation of the pressure regulating means, the flow impedance parameter, and the pressure within the conduit means.

2. An apparatus for assisting in ventilating the lungs of a patient according to claim 1 in which the flow impedance parameter is defined by the following equation:

$$\alpha = \frac{P^{1/2}}{Q}$$

where

α: flow impedance parameter

P: pressure within the conduit

Q: flow rate of the respiratory gas.

3. An apparatus for assisting in ventilating the lungs of a patient according to claim 1 in which the means for predicting the flow impedance parameter comprises a means for storing a preceding value of the flow impedance parameter and the present value of the flow impedance parameter; and the predicted flow impedance parameter being calculated by a first order extrapolation based on the preceding and present values of the flow impedance parameter.

4. An apparatus for assisting in ventilating the lungs of a patient according to claim 1 in which the means for predicting the flow impedance parameter comprises a means for storing a plurality of preceding values of the parameter and the present value of the flow impedance parameter; and the predicted flow impedance parameter being calculated by an extrapolation higher than or equal to the second order based on the plurality of preceding values and present value of the flow impedance parameter.

5. An apparatus for assisting in ventilating the lungs of a patient according to claim 1 further comprising a means for determining whether the respiration is in the expiration phase or in the inspiration phase.

6. An apparatus for assisting in ventilating the lungs of a patient according to claim 5 in which the means for determining the respiration phase comprises a means for comparing the pressure detected by the pressure sensor means with the target pressure;

a means for differentiating the flow rate of the respiratory gas;

a means for comparing the differential flow rate with a predetermined value; and the expiration phase being determined when the detected pressure is higher than the target pressure and the differential flow rate is lower than the predetermined value.

7. An apparatus for assisting in ventilating the lungs of a patient according to claim 5 in which the means for determining the respiration phase comprises:

a means for comparing the pressure detected by the pressure sensor means with the target pressure;

a means for differentiating the flow rate of the respiratory gas;

a means for comparing the differential flow rate with a predetermined value;

a means for differentiating the pressure detected by the pressure sensor;

a means for comparing the differential pressure with a predetermined value; and the expiration phase being determined when the detected pressure is higher than the target pressure, the differential flow rate is lower than the predetermined value, and the differential pressure is higher than the predetermined value.

8. An apparatus for assisting in ventilating the lungs of a patient according to claim 6 further comprising an expiratory valve means for exhausting the expiratory gas from the patient, the expiratory valve means being provided in the conduit means downstream of the pressure regulating means.

9. An apparatus for assisting in ventilating the lungs of a patient according to claim 8 in which the expiratory valve means comprises a first expiratory valve provided in the conduit means downstream of and near the pressure regulating means, and a second expiratory valve provided in the conduit means upstream of the pressure sensor means and near the breathing mask;

the apparatus further comprising a means for comparing the pressure detected by the pressure sensor means with a predetermined pressure level; and the first expiratory valve being open during the expiration phase, the second expiratory valve means being open when the expiration phase is initiated and being closed when the detected pressure is equal to or lower than the predetermined pressure level.

10. An apparatus for assisting in ventilating the lungs of a patient according to claim 9 in which the pressure regulating means comprises a motor operated butterfly valve provided in the conduit means, the butterfly valve being closed when the expiration phase is initiated, after which the butterfly valve is kept closed until the detected pressure becomes equal to or lower than the predetermined level, and after which, and during the inspiration phase, the degree of the opening of the butterfly valve is controlled.

11. An apparatus for assisting in ventilating the lungs of a patient according to claim 10 in which the motor operated butterfly valve has an inlet port which is connected to the outlet port of the respiratory gas source means, and an outlet port which is connected to the inlet of the breathing mask.

12. An apparatus for assisting in ventilating the lungs of a patient according to claim 10 in which the motor operated butterfly valve has an inlet port which is connected to the outlet of the respiratory gas source means and to the inlet of the breathing mask, and an outlet port which is open to the environment.

13. An apparatus for assisting in ventilating the lungs of a patient comprising:

a respiratory gas source means for supplying the respiratory gas to a patient;

a breathing mask means for introducing the respiratory gas into the lungs of a patient, the breathing mask being suitable to be put on the face of a patient;

a conduit means for fluidly connecting the respiratory gas source means to the breathing mask for delivering the respiratory gas from the respiratory gas source means to the breathing mask;

a means for regulating the pressure within the conduit means;

an expiratory valve means for exhausting the expiratory gas from the patient, the expiratory valve means being provided in the conduit means downstream of the pressure regulating means;

a flow meter means for detecting the flow rate of the respiratory gas from the respiratory gas source to the breathing mask;

a pressure sensor means for detecting the pressure within the conduit adjacent to the breathing mask;

a means for determining whether the respiration is the expiration phase or in the inspiration phase;

a means for obtaining a flow impedance parameter of the flow system downstream of the pressure sensing means including the airways and the lungs of a patient based on the flow rate and pressure detected by the flow meter and the pressure sensor means;

the flow impedance parameter being defined by the following equation;

$$\alpha = \frac{P^{1/2}}{Q}$$

where
- $\alpha$: flow impedance parameter
- P: pressure within the conduit
- Q: flow rate of the respiratory gas a means for storing the relationship between the operation of the pressure regulating means, the flow impedance parameter, and the pressure within the conduit means;

a means for predicting the flow impedance parameter after a predetermined time interval;

a means for generating a target pressure signal to which the pressure regulating means regulates the pressure within the conduit; and a means for controlling the operation of the pressure regulating means such that the pressure within the conduit adjacent to the breathing mask becomes substantially the target pressure based on the predicted flow impedance parameter and the relationship between the operation of the pressure regulating means, the flow impedance parameter, and the pressure within the conduit means.

14. An apparatus for assisting in ventilating the lungs of a patient according to claim 13 in which the means for predicting the flow impedance parameter comprises a means for storing a preceding value of the parameter and the present value of the parameter; and the predicted flow impedance parameter being calculated by a first order extrapolation based on the preceding and present values of the impedance parameter.

15. An apparatus for assisting in ventilating the lungs of a patient according to claim 13 in which the means for predicting the flow impedance parameter comprises a means for storing a plurality of preceding values of the parameter and the present value of the parameter; and the predicted flow impedance parameter being calculated by an extrapolation higher than or equal to the second order based on the plurality of preceding values and present value of the impedance parameter.

16. An apparatus for assisting in ventilating the lungs of a patient according to claim 13 in which the means for determing the respiration phase comprises a means for comparing the pressure detected by the pressure sensor means with the target pressure;

a means for differentiating the flow rate of the respiratory gas;

a means for comparing the differential flow rate with a predetermined value; and the expiration phase being determined when the detected pressure is higher than the target pressure and the differential flow rate is lower than the predetermined value.

17. An apparatus for assisting in ventilating the lungs of a patient according to claim 13 in which the means for determining the respiration phase comprises:

a means for comparing the pressure detected by the pressure sensor means with the target pressure;

a means for differentiating the flow rate of the respiratory gas;

a means for comparing the differential flow rate with a predetermined value;

a means for differentiating the pressure detected by the pressure sensor;

a means for comparing the differential pressure with a predetermined value; and the expiration phase being determined when the detected pressure is higher than the target pressure, the differential flow rate is lower than the predetermined value, and the differential pressure is higher than the predetermined value.

18. An apparatus for assisting in ventilating the lungs of a patient according to claim 13 in which the expiratory valve means comprises a first expiratory valve provided in the conduit means downstream of and near the pressure regulating means, and a second expiratory valve provided in the conduit means upstream of the pressure sensor means and near the breathing mask;

the apparatus further comprising a means for comparing the pressure detected by the pressure sensor means with a predetermined pressure value; and the first expiratory valve being open during the expiration phase, the second expiratory valve means being open when the expiration phase is initiated and being closed when the detected pressure is lower than the predetermined pressure value.

19. An apparatus for assisting in ventilating the lungs of a patient according to claim 13 in which the pressure regulating means comprises a motor operated butterfly valve provided in the conduit means, the butterfly valve being closed when the expiration phase is initiated, after which the butterfly valve is kept closed until the detected pressure becomes equal to or lower than the predetermined level, and after which, and during the inspiration phase, the degree of the opening of the butterfly valve is controlled.

20. An apparatus for assisting in ventilating the lungs of a patient according to claim 19 in which the motor operated butterfly valve has an inlet port which is connected to the outlet port of the respiratory gas source means, and an outlet port which is connected to the inlet of the breathing mask.

21. An apparatus for assisting in ventilating the lungs of a patient according to claim 19 in which the motor operated butterfly valve has an inlet port which is connected to the outlet of the respiratory gas source means and to the inlet of the breathing mask, and an outlet port which is open to the environment.

* * * * *